(12) United States Patent
Turner et al.

(10) Patent No.: US 6,340,680 B1
(45) Date of Patent: Jan. 22, 2002

(54) OXAZINOQUINOLONES USEFUL FOR THE TREATMENT OF VIRAL INFECTIONS

(75) Inventors: Steven Ronald Turner; Suvit Thaisrivongs, both of Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/672,472

(22) Filed: Sep. 28, 2000

Related U.S. Application Data

(60) Provisional application No. 60/157,742, filed on Oct. 5, 1999.

(51) Int. Cl.$^7$ .................. C07D 498/06; C07D 516/04; A61K 35/535; A61K 35/54
(52) U.S. Cl. ..................................... 514/230.2; 544/101
(58) Field of Search ........................ 544/101; 514/230.2

(56) References Cited

U.S. PATENT DOCUMENTS

| 4,568,649 A | 2/1986 | Bertglio-Matte ............ 436/534 |
| 4,847,373 A | 7/1989 | Baker et al. ................ 540/215 |
| 5,583,135 A | 12/1996 | Matsuo et al. ............ 514/230.2 |
| 5,792,774 A | 8/1998 | Haughan et al. ............. 514/294 |

FOREIGN PATENT DOCUMENTS

| WO | WO 98/11073 | 3/1998 | ......... C07D/215/48 |

OTHER PUBLICATIONS

Abstract of Japanese Patent JP 10324631-A.

*Primary Examiner*—Bruck Kifle
(74) *Attorney, Agent, or Firm*—Lucy X. Yang

(57) ABSTRACT

The present invention provides a compound of formula I

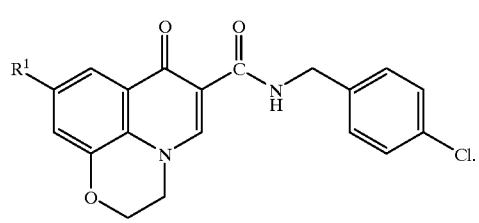

These compounds are useful as antiviral agents, in particular, as agents against viruses of the herpes family.

9 Claims, No Drawings

OXAZINOQUINOLONES USEFUL FOR THE TREATMENT OF VIRAL INFECTIONS

CROSS REFERENCE TO RELATED APPLICATIONS

This application claims the benefit of U.S. Ser. No. 60/157,742, filed Oct. 5, 1999, under 35 USC 119(e)(i).

FIELD OF THE INVENTION

The present invention provides oxazinoquinolone derivatives having a ring connecting position 4 (N-4) and position 11 (C-11), and more specifically, provides compounds of formula (I) described herein below. These compounds are useful as antiviral agents, in particular, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and (HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Due to the unique position of chloro substitutent on the N-phenylmethyl of formula I described herein below, compounds of the present invention demonstrate unexpected activity against the above reference herpesviral infections, particularly, human cytomegaloviral infection.

INFORMATION DISCLOSURE

U.S. Pat. No. 5,792,774 discloses oxazino 1,4-dihydro-4-oxoquinolines useful for the treatment of a large number of diseases modulated by tissue necrosis factor (TNF) or phosphodiesterase IV, including cytomegalovirus (CMV) infections.

U.S. Pat. No. 4,847,373 discloses 1,8-bridged 4-quinoline-3-carboxylic acids useful as antibacterial agents.

U.S. Pat. No. 5,583,135 discloses heterotricyclic derivatives having a strong immunomodulating activity, anti-inflammatory activity and anti-cancer activity.

The abstract of Japanese Patent JP 10324631-A discloses IgE antibody production inhibitor comprise a pyrido(1,2,3-de1,4-benzoxazine or a pyrido (1,2,3-de)-1,4-benzothiazine derivative.

SUMMARY OF THE INVENTION

The present invention provides a compound of formula I,

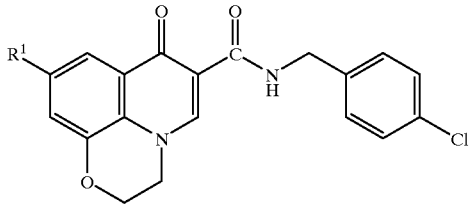

I wherein $R^1$ is $C_{1-6}$ alkyl, optionally substituted with —OH, —$OC_{1-4}$ alkyl or het;
wherein $C_{1-6}$ alkyl is optionally partially unsaturated;
wherein het is a radical of a five- or six-membered heterocyclic ring having one or two heteroatoms selected from the group consisting of oxygen, sulfur and N; or a pharmaceutically acceptable salt, racemate, solvate, tautomer, optical isomer or prodrug derivative thereof.

In another aspect, the present invention also provides:
a pharmaceutical composition comprising a compound of formula I, or a pharmaceutically acceptable salt thereof, and a pharmaceutically acceptable excipient (the composition preferably comprises an effective antiviral amount of the compound or salt),
a method of treating or preventing a herpesviral infection, comprising administering to a mammal (e.g. a human) in need of such treatment, a compound of formula (I) or a pharmaceutically acceptable salt thereof,
a compound of formula (I) or a pharmaceutically acceptable salt thereof for use in medical treatment (e.g. the treatment or prevention of a herpesviral infection),
the use of a compound of formula (I) or a pharmaceutically acceptable salt thereof to prepare a medicament for treating or preventing a herpesviral infection in a mammal (e.g. a human), and
a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, or methyl, ethyl, propyl and isopropyl, straight and branched forms thereof.

The compounds of the present invention are named according to the IUPAC or CAS nomenclature system.

The term "$C_{1-6}$", " refers to an alkyl group having one to six carbon atoms such as, for example, methyl, ethyl, propyl, butyl, pentyl, hexyl, and their isomeric forms thereof.

A 5- or 6-membered heterocyclic ring includes pyridinyl, morpholinyl, thiomorpholinyl, piperazinyl, imidazolyl, or pyrrolyl.

Compounds of the present invention may be in a form of pharmaceutically acceptable salts.

"Pharmaceutically acceptable salts" refers to those salts which possess the biological effectiveness and properties of the parent compound and which are not biologically or otherwise undesirable.

Compounds of the invention may have a chiral center and be isolated in optically active and racemic forms. It is to be understood that the present invention encompasses any racemic, optically-active, polymorphic, tautomeric, or stereoisomeric form, or mixture thereof.

Specific and preferred values listed below for radicals, substituents, and ranges, are for illustration only; they do not exclude other defined values or other values within defined ranges for the radicals and substituents Specifically, $C_{1-6}$ alkyl can be methyl, ethyl, propyl, isopropyl, butyl, iso-butyl, sec-butyl, pentyl, 3-pentyl, hexyl, or heptyl; het can be pyrrolidino, piperidino, morpholino, thiomorpholino, or piperazine.

A specific value for $R^1$ is $C_{1-6}$ alkyl, which may be partially unsaturated and is optionally substituted by hydroxy or het.

A specific value for $R^1$ is propyl.

A specific value for $R^1$ is 3-hydroxypropyl.

A specific value for $R^1$ is 3-hydroxy-1-propynyl.

A specific value for $R^1$ is 4-morpholinylmethyl.

Examples of the present invention are:
a. N-(4-Chlorobenzyl)-9-(4-morpholinylmethyl)-7-oxo-2,3-dihydro-7H-[1,4]oxazino[2,3,4-ij]quinoline-6-carboxamide,
b. N-(4-Chlorobenzyl)-9-(3-hydroxy-1-propynyl)-7-oxo-2,3-dihydro-7H-[1,4]oxazino[2,3,4-ij]quinoline-6-carboxamide,
c. N-(4-Chlorobenzyl)-9-(3-hydroxypropyl)-7-oxo-2,3-dihydro-7H-[1,4]oxazino[2,3,4-ij]quinoline-6-carboxamide, or
d. N-(4-Chlorobenzyl)-7-oxo-9-propyl-2,3-dihydro-7H-[1,4]oxazino[2,3,4-ij]quinoline-6-carboxamide.

The following Charts A–B describe the preparation of the compounds of formula I of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry. All of the variables used in the charts are as defined below or as in the claims.

In Chart A, acid A-1,3-hydroxy-4-nitrobenzoic acid, is reacted with thionyl chloride to give the corresponding acid chloride, which is then treated with morpholine to provide amide A-2. Alkylation of the phenolic hydroxyl group is accomplished using methyl bromoacetate and potassium carbonate in refluxing acetone to give A-3. Reduction of the nitro group using hydrogen gas and catalytic palladium, followed by thermal cyclization of the intermediate amino ester, provides lactam A-4. Reduction of the lactam with lithium aluminum hydride affords amine A-5. Reaction of the amine with diethyl ethoxymethylenemalonate provides A-6, which is heated with polyphosphoric acid or a solution of phosphorus pentoxide in methanesulfonic acid, effecting cyclization to tricyclic ester A-7. Aminolysis of the ester using p-chlorobenzylamine at 150° C. provides amide A-8.

CHART A

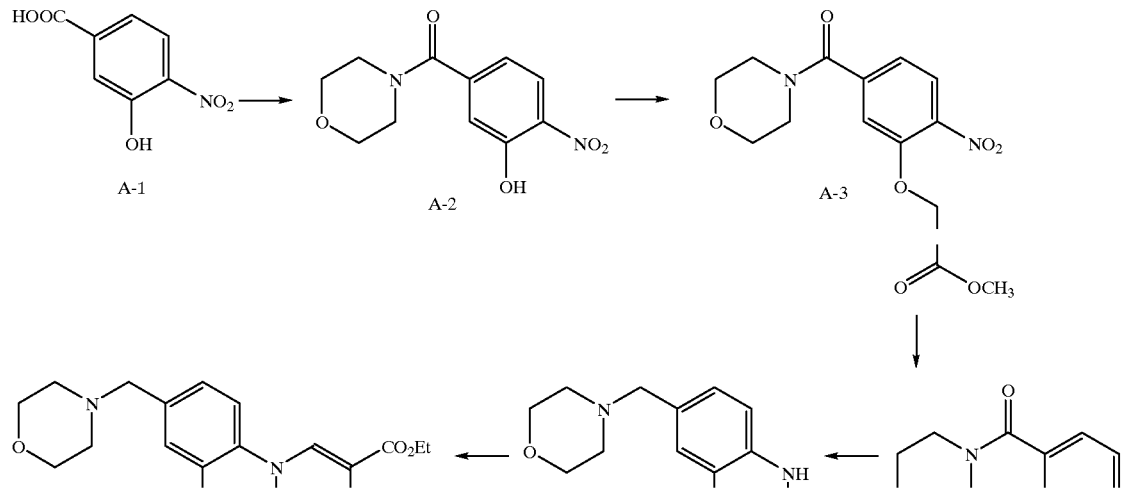

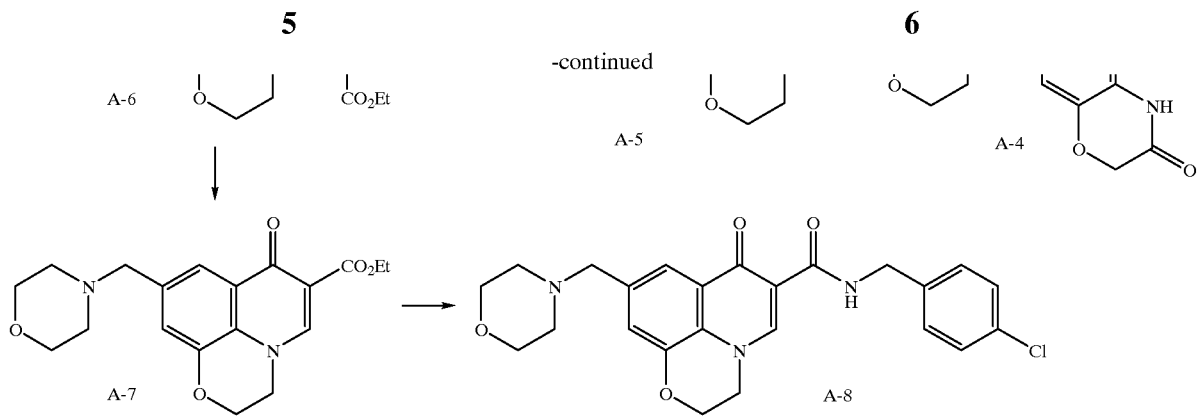

In Chart B, deprotonation of B-1, 3,4-difluoroiodobenzene, with lithium diisopropylamide in tetrahydrofuran, followed by quenching of the anion with carbon dioxide, provides regioisomeric mixture of acids B-2. Activation of the acid mixture with carbonyldiimidazole, followed by reaction of the imidazolide with ethyl trimethylsilyl malonate in the presence of base affords the single β-ketoester B-3. Sequential treatment of the β-ketoester with triethyl orthoformate and ethanolamine affords compound B-4, which is cyclized using potassium carbonate in DMF to provide tricyclic ester B-5. Aminolysis of the ethyl ester using p-chlorobenzylamine furnishes amide B-6, which is converted to alkynol derivative B-7 by palladium (II) catalyzed coupling of the iodide with propargyl alcohol. Catalytic hydrogenation of the alkyne using hydrogen gas and platinum on carbon provides hydroxypropyl compound B-8 and n-propyl analogue B-9.

CHART B

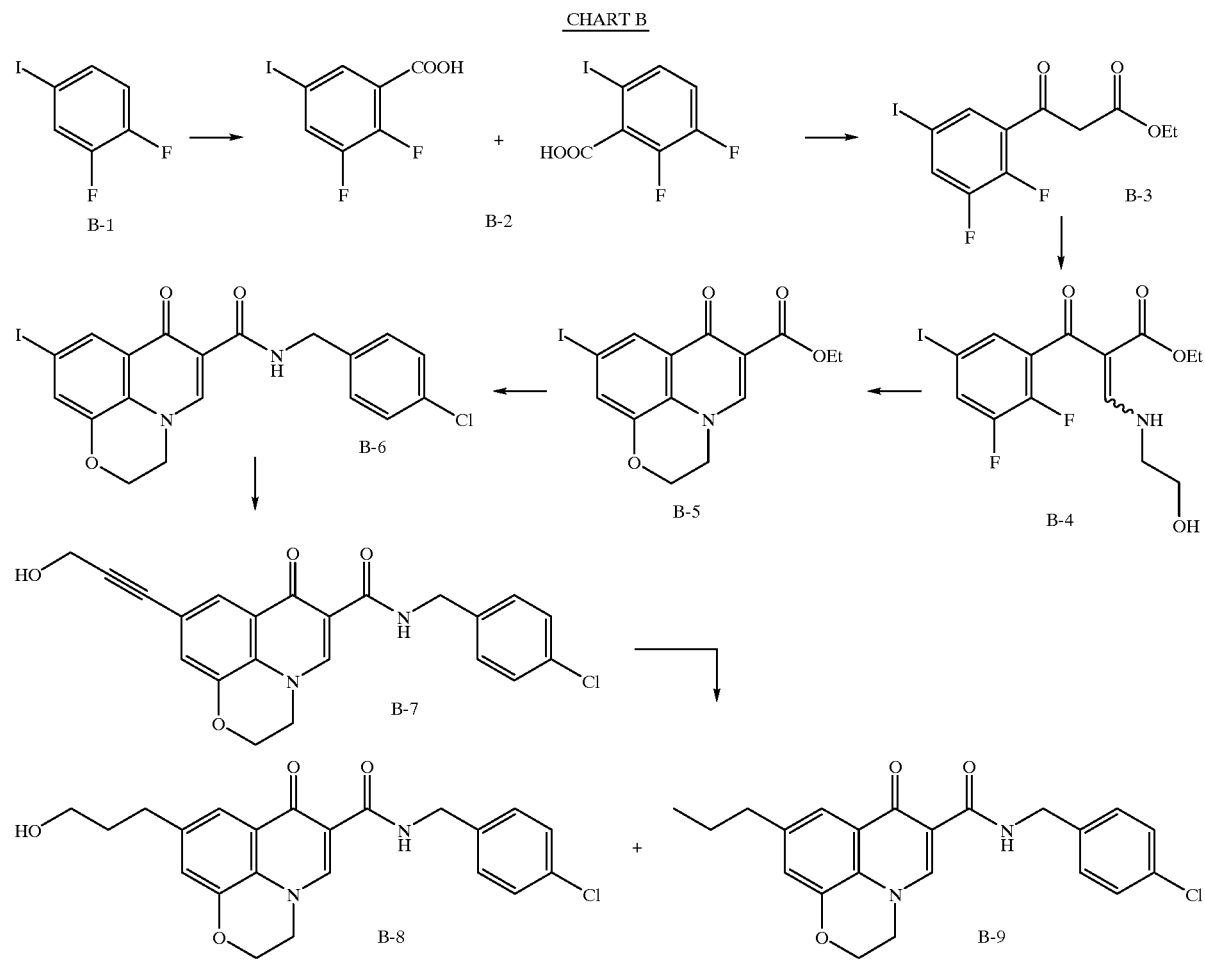

It will be apparent to those skilled in the art that the described synthetic procedures are merely representative in nature and alternative synthetic processes are known to one of ordinary skill in organic chemistry.

The compounds of the present invention and pharmaceutically acceptable salts thereof are useful as antiviral agents. Thus, these compounds are useful to combat viral infections in animals, including man. Specifically, these compounds have anti-viral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

Also, while many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C or 37 C $H_2O$ bath and terminated via the addition of 40 µl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37 C, then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of compounds of the present invention in this assay are shown in Tables 1 below. Other viral polymerase assays are performed using procedures similar to those described above.

These compounds of the present invention are administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975), which is hereby incorporated by reference herein.

The compounds of the present invention are administered parenterally (for example, by intravenous, intraperitoneal or intramuscular injection), topically, orally, or rectally, depending on whether the preparation is used to treat internal or external viral infections.

For internal infections, the compositions are administered orally or parenterally at dose levels, calculated as the free base, of about 0.1 to 300 mg/kg, preferably 1.0 to 30 mg/kg of mammal body weight, and are used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to 10%, more preferably about 0.1 to 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

TABLE 1

| | polymerase $IC_{50}$ (µM) | | |
|---|---|---|---|
| Example No. | HCMV | HSV | VZV |
| 1 | 0.48 | — | — |
| 2 | 1.2 | — | — |
| 3A | <0.31 | 0.44 | 0.21 |
| 3B | 1.8 | — | — |

The symbol "—" refers to the data are not determined

The symbol "--" refers to the data are not determined.

The compounds and their preparation of the present invention will be better understood in connection with the following examples, which are intended as an illustration of and not a limitation upon the scope of the invention.

EXAMPLES

Preparation 1 (3-Hydroxy-4-nitrophenyl)(4-morpholinyl) methanone (A-2 of Chart A)

To a stirred mixture of 55.0 g of 3-hydroxy-4-nitrobenzoic acid in 600 ml of dichloromethane is added 35 ml of thionyl chloride and 5.0 ml of DMF. The mixture is stirred and refluxed with exclusion of moisture for 1–2 hours, when it suddenly becomes a clear solution. Refluxing is continued for another hour, then volatiles are removed under reduced pressure. The residual amber oil is dissolved in dichloromethane (200 ml), toluene (200 ml) is added, and the solution again concentrated under reduced pressure. The resulting amber oil is dissolved in 300 ml of dichloromethane, and to this solution, stirred and cooled to 0° C., is added dropwise 65 ml of morpholine in 200 ml of dichloromethane. The resulting mixture is stirred overnight, then washed with water containing sufficient 6N HCl to render the aqueous phase acidic. The aqueous phase is extracted with one additional portion (100 ml) of dichloromethane, and the combined extracts dried ($Na_2SO_4$) and concentrated under reduced pressure, affording an orange solid. Recrystallization from 1:3 ethyl acetate in heptane provides 70.34 g of the title compound.

Mp 105.5–106.5° C.; $^1$H NMR ($CDCl_3$) δ 3.40, 3.64, 3.79, 7.01, 7.18, 8.18, 10.63 ppm; HRMS (FAB) calcd for $C_{11}H_{12}N_2O_5$+$H_1$ 253.0824, found 253.0832. Anal. Calcd for $C_{11}H_{12}N_2O_5$: C, 52.38; H, 4.80; N, 11.11; Found: C, 52.46; H, 4.85; N, 11.11.

Preparation 2 Methyl 2-[5-(4-Morpholinylcarbonyl)-2-nitrophenoxy]acetate (A-3 of Chart A)

A mixture of 70.05 g of 3-hydroxy-4-nitrophenyl)(4-morpholinyl)methanone of Preparation 1, 42.2 g of anhydrous potassium carbonate, and 28.9 ml of methyl bromoacetate in 700 ml of acetone is stirred and refluxed for 5 hours. Solvents are then removed under reduced pressure, and the residual solid is partitioned between dichloromethane (300 ml) and water (300 ml) containing sufficient 6N HCl to render the aqueous phase acidic. The aqueous phase is extracted with one additional portion (100 ml) of dichloromethane, and the combined organic phases dried ($Na_2SO_4$) and concentrated under reduced pressure. Recrystallization of the residue from ethyl acetate and heptane furnishes 85.53 g of the title compound.

Mp 140.5–142° C.; $^1$H NMR ($CDCl_3$) δ 3.40, 3.63, 3.78, 3.81, 4.83, 7.04, 7.11, 7.90 ppm; IR 1759, 1637, 1608, 1591, 1525, 1436, 1303, 1213, 1114, 842cm$^{-1}$. Anal. Calcd for $C_{14}H_{16}N_2O_7$: C, 51.85; H, 4.97; N, 8.64; Found: C, 51.87; H, 5.06; N, 8.61.

Preparation 3 7-(4-Morpholinylcarbonyl)-2H-1,4-benzoxazin-3(4H)-one (A-4 of Chart A)

Methyl 2-[5-(4-morpholinylcarbonyl)-2-nitrophenoxy]acetate of Preparation 2 (85.2 g) is hydrogenated in two batches. Approximately half of the compound is shaken in 600 ml of methanol with 1 g of 5% palladium on charcoal under 20 psi $H_2$. Shaking under hydrogen is continued for 1 hour after hydrogen uptake ceases. The combined reaction mixtures from two such reductions are refluxed under argon for 5 hours, then cooled to 35° C. and filtered through a pad of Celite. Concentration of the filtrate under reduced pressure provides a yellow-white solid residue, which is recrystallized from 800 ml of acetonitrile to afford 62.32 g of the title compound.

Mp 185.5–187.5° C.; $^1$H NMR ($CDCl_3$) δ 3.70, 4.64, 6.89, 7.03, 9.66 ppm; IR 1705, 1617, 1461, 1432, 1284, 1114, 1025, 729 cm$^{-1}$. HRMS (FAB) calcd for $C_{13}H_{14}N_2O_4$+$H_1$ 263.1031, found 263.1025. Anal. Calcd for $C_{13}H_{14}N_2O_4$: C, 59.54; H, 5.38; N, 10.68; Found: C, 59.29; H, 5.40; N, 10.63.

Preparation 4 7-(4-Morpholinylmethyl)-3,4-dihydro-2H-1,4-benzoxazine (A-5 of Chart A)

To an ice-cooled suspension of 26.2 g of 7-(4-morpholinylcarbonyl)-2H-1,4-benzoxazin-3(4H)-one of Preparation 3 in 350 ml of dry THF under argon is added in portions 7.6 g of lithium aluminum hydride. The completed mixture is stirred while the temperature of the reaction is allowed to rise slowly to ambient as the ice in the cooling bath melts. The reduction is allowed to proceed overnight, then the reaction is re-cooled to 0° C. and quenched by the cautious sequential addition of 7 ml of water dissolved in 15 ml of THF, 7 ml of 3N NaOH, and 21 ml of water.

Dichloromethane (350 ml) and anhydrous $Na_2SO_4$ (10 g) are added, and the mixture stirred vigorously for 20 minutes. The mixture is then filtered, and the solid washed with several portions of dichloromethane. The filtrate is concentrated under reduced pressure to provide 24.98 g of the title compound.

$^1$H NMR ($CDCl_3$) δ 2.42, 3.35, 3.41, 3.68, 4.24, 6.54, 6.69, 6.75 ppm; IR 3370, 2854, 1518, 1350, 1295, 1115, 1006, 863 cm$^{-1}$. EI MS m/z 235

Preparation 5 Ethyl 9-(4-morpholinylmethyl)-7-oxo-2,3-dihydro-7H-[1,4]oxazino[2,3,4-ij]quinoline-6-carboxylate (A-7 of Chart A)

A mixture of 9.37 g of 7-(4-morpholinylmethyl)-3,4-dihydro-2H-1,4-benzoxazine of Preparation 4 and 10.4 g of diethyl ethoxymethylenemalonate is stirred and heated at 140° C. for 2 hours. During this time, ethanol formed in the reaction is removed through a distillation apparatus attached to the reaction flask. The reaction is then cooled under vacuum to afford the enamine intermediate A-6 as a yellow oil. This is dissolved in 20 ml of dichloromethane and added to a stirred solution of 8.5 g of phosphorus pentoxide in 52 ml of methanesulfonic acid. The reaction temperature is kept below 30° C. during the addition by controlling the rate of addition and by external cooling of the flask. The completed mixture is heated at 50° C. for 18 hours and then cooled to 0° C., diluted with dichloromethane and water, and cautiously made alkaline by addition of 10M NaOH. Phases are separated and the aqueous extracted with two additional portions of dichloromethane. The combined extract is dried ($Na_2SO_4$) and concentrated under reduced pressure to afford a tan solid. Recrystallization from acetonitrile provides 10.0 g of the title compound.

Mp 216–218° C.; $^1$H NMR ($CDCl_3$) δ 1.40, 2.44, 3.55, 3.70, 4.27, 4.37, 4.50, 7.28, 7.94, 8.30 ppm; IR 1722, 1689, 1601, 1556, 1504, 1318, 1290, 1247, 1117, 1070, 1032, 880, 807 cm$^{-1}$. Anal. Calcd for $C_{19}H_{22}N_2O_5$: C, 63.67; H, 6.19; N, 7.82; Found: C, 63.52; H, 6.21; N, 7.80.

Example 1

N-(4-Chlorobenzyl)-9-(4-morpholinylmethyl)-7-oxo-2,3-dihydro-7H-[1,4]oxazino[2,3,4-ij]quinoline-6-carboxamide (A-8 of Chart A) [PNU-2469621]

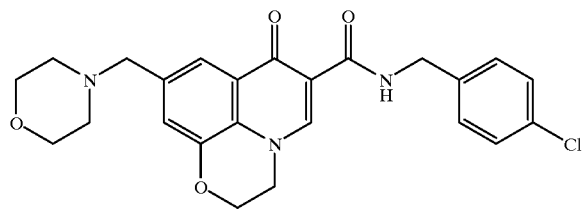

A mixture of 4.81 g of ethyl 9-(4-morpholinylmethyl)-7-oxo-2,3-dihydro-7H-[1,4]oxazino[2,3,4-ij]quinoline-6-carboxylate of Preparation 5 and 7.7 g of p-chlorobenzylamine is heated under argon at 150° C. for 18 hours, after which time the bulk of excess amine is distilled off under vacuum. The solid residue is triturated with hexane, filtered and washed with hexane, and dried under vacuum. The resulting solid is chromatographed on silica gel using 2–3% methanol in dichloromethane to provide 5.90 g of the amide as a white solid. Recrystallization from methyl ethyl ketone affords 5.01 g of the title compound.

$^1$H NMR ($CDCl_3$) δ 2.45, 3.58, 3.70, 4.33, 4.51, 4.64, 7.3, 7.94, 8.66, 10.45 ppm; IR (mull) 1651, 1625, 1609, 1558, 1504, 1419, 1316, 1289, 1267, 1116, 1083, 1008, 866, 808, 798 cm$^{-1}$. Anal. Calcd for $C_{24}H_{24}ClN_3O_4$: C, 63.50; H, 5.33; N, 9.26; Cl, 7.81; Found: C, 63.47; H, 5.37; N, 9.22; Cl, 7.82.

Preparation 6 2,3-Difluoro-5-iodobenzoic Acid and 2,3-Difluoro-6-iodobenzoic Acid (B-2 of Chart B)

To a stirred solution of 6.7 mL of diisopropylamine in 80 mL of dry THF, blanketed by argon and cooled to −78° C., is added dropwise 27 mL of a 1.6 M solution of n-butyllithium in hexane. The solution is warmed to 0° C. and held at that temperature for 10 m, then recooled to −78° C. To the solution is added 4.82 mL of 1,2-difluoro-4-iodobenzene, and the solution is stirred for 75 m at −78° C. before being transferred rapidly via cannula to an excess of solid $CO_2$ slurried in ether. The mixture is allowed to warm to room temperature, then is partitioned between ether and dil. NaOH. The aqueous phase is acidified with dil. HCl and the resulting precipitate extracted with dichloromethane. The organic phase is dried over $MgSO_4$ and concentrated under reduced pressure to afford 12.5 g of the mixed acids as a tan oil crystallizing to a solid mass.

$^1$H NMR (CDCl$_3$) δ 6.99, 7.61, 7.71, 8.10 ppm.

Preparation 7 Ethyl 3-(2,3-Difluoro-5-iodophenyl)-3-oxopropanoate (B-3 of Chart B)

To a stirred solution of 11.4 g of difluoroiodobenzoic acid mixture obtained in Preparation 6 in 40 mL of dry THF under argon is added in portions 7.78 g of carbonyldiimidazole and 100 mg of DMAP. The solution is stirred for 18 hours at room temperature. Concurrently, 7.48 g of ethyl potassium malonate is suspended in 40 mL of dry acetonitrile under argon, and to the suspension is added 5.1 mL of chlorotrimethylsilane. The mixture is stirred for 18 h, then cooled to 0° C. for the addition of 12.5 mL of 1,8-diazabicyclo [5.4.0] undec-7-ene. After 1 h, the acyl imidazolide solution is added via cannula, and the resulting mixture is stirred for 1–3 hours. The mixture is then partitioned between ether and excell cold dil. HCl, and the organic phase washed with dil. HCl and brine, and dried (MgSO$_4$). Removal of the solvent under reduced pressure followed by flash chromatography of the residue on silica using 5% ethyl acetate in hepane provides 3.61 g of the title compound as a white crystalline solid.

$^1$H NMR (CDCl$_3$) δ 1.34, 4.28, 5.80, 7.57, 7.95, 12.65 ppm; IR 2989, 1652, 1623, 1490, 1421, 1216, 1037, 960, 800 cm$^{-1}$.

Preparation 8 Ethyl (E,Z)-2-(2,3-Difluoro-5-iodobenzoyl)-3-[(2-hydroxyethyl)amino]-2-propenoate (B-4 of Chart B, R=H)

A solution of 1.77 g of ethyl 3-(2,3-difluoro-5-iodophenyl)-3-oxopropanoate of Preparation 7 and 1.3 mL of triethyl orthoformate in 5 mL of acetic anhydride is refluxed for 3 hours, then concentrated in vacuo to an oil. This is dissolved in 5 mL of ethanol, and to the stirred solution is added 0.60 mL of ethanolamine. The resulting solution is stirred for 18 hours, then concentrated under reduced pressure. Flash chromatography of the residual oil on silica using 50–75% ethyl acetate in dichloromethane provides 2.06 g of the title compound.

$^1$H NMR (CDCl$_3$) δ 0.93, 1.04, 3.3, 3.56, 3.76, 3.9–4.2, 7.37, 7.49, 8.17, 9.75, 10.50 ppm; IR 3400, 2982, 1676, 1635, 1481, 1430, 1313, 1215, 1056 cm$^{-1}$.

Preparation 9 Ethyl 9-Iodo-7-oxo-2,3-dihydro-7H-[1,4] oxazino[2,3,4-ij]quinoline-6-carboxylate (B-5 of Chart B, R=H)

A stirred mixture of 883 mg of ethyl (E,Z)-2-(2,3-difluoro-5-iodobenzoyl)-3-[(2-hydroxyethyl)amino]-2-propenoate of Preparation 8 and 630 mg of powdered potassium carbonate in 10 mL of DMF is heated at 95° C. for 3.5 hours, then cooled and added to 120 mL of water containing 4 mL of 6N HCl. The precipitated product is extracted with chloroform, and the organic phase dried (MgSO$_4$) and concentrated under reduced pressure. Flash chromatography of the residue on silica using 2% methanol in dichloromethane affords 580 mg of the title compound. An analytical sample may be prepared by recrystallization from acetonitrile.

Mp ~270° C.; $^1$H NMR (CDCl$_3$+CD$_3$OD) δ 1.40, 4.32, 4.37, 4.51, 7.54, 8.31, 8.38; IR 3077, 1718, 1626, 1576, 1552, 1283, 1252, 1158, 800, 719 cm$^{-1}$; HRMS (m+H) 385.9908; Anal. Found for $C_{14}H_{12}NO_4I$: C, 43.57; H, 3.24; N, 3.63.

Preparation 10 N-(4-Chlorobenzyl)-9-iodo-7-oxo-2,3-dihydro-7H-[1,4]oxazino[2,3,4-ij]quinoline-6-carboxamide (Formula B-6 of Chart B, R=H)

A mixture of 575 mg of ethyl 9-iodo-7-oxo-2,3-dihydro-7H-[1,4]oxazino[2,3,4-ij]quinoline-6-carboxylate of Preparation 9 and 2.0 g of p-chlorobenzylamine is heated at 160° C. for 16 hours, then cooled and treated with 20 mL of 1N HCl. After 30 minutes of vigorous stirring, the solid is filtered, washed well with water, and dried in vacuo. The solid is further triturated with ether and dichloromethane to afford 563 mg of the title compound as a pale coral solid.

$^1$H NMR (CDCl$_3$+CD$_3$OD+TFA) δ 4.43, 4.53, 4.64, 7.32, 7.63, 8.32, 8.76 ppm; HRMS (m+H) 480.9828; Anal. Found for $C_{19}H_{14}N_2O_3ClI$: C, 47.55; H, 2.89; N, 5.74.

Example 2

N-(4-Chlorobenzyl)-9-(3-hydroxy-1-propynyl)-7-oxo-2,3-dihydro-7H-[1,4]oxazino[2,3,4-ij]quinoline-6-carboxamide (B-7 of Chart B, R=H)

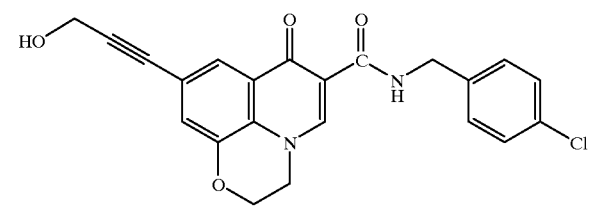

To a mixture of 539 mg of N-(4-chlorobenzyl)-9-iodo-7-oxo-2,3-dihydro-7H-[1,4]oxazino[2,3,4-ij]quinoline-6-carboxamide of Preparation 10, 78 mg of copper (I) odide, and 30 mg of bis(triphenylphosphine)palladium dichloride in 11 mL of diethylamine, stirred vigorously under argon, is added 82 μL of propargyl alcohol. The mixture is stirred for 18 hours, then diluted with a little methanol and added to 120 mL of stirred water. The precipitated solid is filtered, washed well with water, and dried in vacuo. The solid is then dissolved in chloroform-methanol, and the solution is filtered to remove copper salts and then absorbed onto silica gel. Flash chromatography eluting with 2–6% methanol in dichloromethane provides 217 mg of the title compound.

$^1$H NMR (CDCl$_3$+CD$_3$OD) δ 4.39, 4.44, 4.52, 4.63, 7.21, 7.32, 7.91, 8.61 ppm; IR 1643, 1569, 1490, 1450, 1296, 1230, 1087, 1025, 902, 874, 803, 731 cm$^{-1}$; HRMS (m+H) 409.0952.

Example 3A and 3B

N-(4-Chlorobenzyl)-9-(3-hydroxypropyl)-7-oxo-2,3-dihydro-7H-[1,4]oxazino[2,3,4-ij]quinoline-6-carboxamide (3A) and N-(4-Chlorobenzyl)-7-oxo-9-propyl-2,3-dihydro-7H-[1,4]oxazino[2,3,4-ij]quinoline-6-carboxamide (3B) (B-8 and B-9 of Chart B)

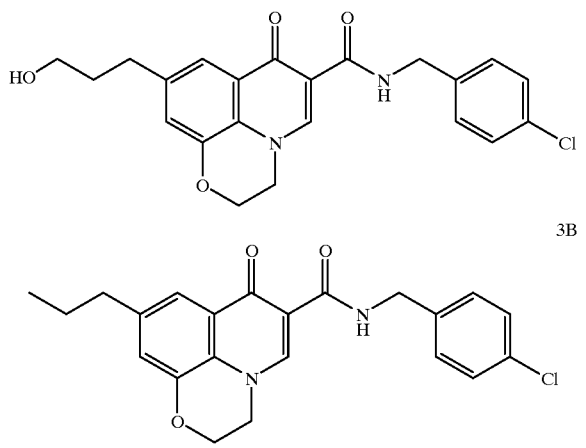

A mixture of 50 mg of N-(4-chlorobenzyl)-9-(3-hydroxy-1-propynyl)-7-oxo-2,3-dihydro-7H-[1,4]oxazino[2,3,4-ij]quinoline-6-carboxamide of Example 2 and 20 mg of 5% platinum on carbon in 2 mL of 1:1 THF-methanol is stirred vigorously under 1 atmosphere of hydrogen gas for 3 hours, then filtered through diatomaceous earth. The filtrate is concentrated under reduced pressure, and the residue chromatographed on silica using 2–3% methanol in dichloromethane. Following concentration under reduced pressure, the upper eluting fractions provide 16.5 mg of N-(4-chlorobenzyl)-7-oxo-9-propyl-2,3-dihydro-7H-[1,4]oxazino[2,3,4-ij]quinoline-6-carboxamide (3B); the lower eluting fractions similarly afford 27.5 mg of N-(4-chlorobenzyl)-9-(3-hydroxypropyl)-7-oxo-2,3-dihydro-7H-[1,4]oxazino[2,3,4-ij]quinoline-6-carboxamide (3A).

Physical Characteristics for 3A are as Follows:

$^1$H NMR (CDCl$_3$) δ 1.9, 2.82, 3.62, 4.38, 4.51, 4.63, 7.16, 7.31, 7.82, 8.63; IR 3349, 2937, 1647, 1608, 1557, 1504, 1453, 1286, 1053, 805 cm$^{-1}$; HRMS (m+H) 413.1266.

Physical Characteristics for 3B are as Follows:

Mp 205–206° C.; $^1$H NMR (CDCl$_3$) δ 0.94, 1.7, 2.69, 4.31, 4.49, 4.63, 7.11, 7.3, 7.83, 8.64, 10.5 ppm; IR 3040, 2929, 1651, 1609, 1558, 1504, 805 cm$^{-1}$; HRMS (m+H) 397.1316; Anal. Found for C$_{22}$H$_{21}$N$_2$O$_3$Cl: C, 66.35; H, 5.37; N, 7.03.

We claim:

1. A compound of formula I

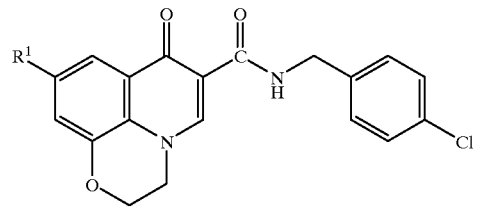

wherein R$^1$ is C$_{1-6}$ alkyl, optionally substituted with —OH, —OC$_{1-4}$ alkyl or het;

wherein C$_{1-6}$ alkyl is optionally partially unsaturated;

wherein het is a radical of a five- or six-membered heterocyclic ring having one or two heteroatoms selected from the group consisting of oxygen, sulfur and N;

or a pharmaceutically acceptable salt, racemate, solvate, tautomer or optical isomer thereof.

2. A compound of claim 1 wherein R$^1$ is propyl.

3. A compound of claim 1 wherein R$^1$ is 3-hydroxypropyl.

4. A compound of claim 1 wherein R$^1$ is 3-hydroxy-1-propynyl.

5. A compound of claim 1 wherein het is morpholine, thiomorpholine, piperidine, piperazine or pyrrolidine.

6. A compound of claim 1 wherein R$^1$ is 4-morpholinylmethyl.

7. A compound of claim 1 which is (a) N-(4-Chlorobenzyl)-9-(4-morpholinylmethyl)-7-oxo-2,3-dihydro-7H-[1,4]oxazino[2,3,4-ij]quinoline-6-carboxamide, (b) N-(4-Chlorobenzyl)-9-(3-hydroxy-1-propynyl)-7-oxo-2,3-dihydro-7H-[1,4]oxazino[2,3,4-ij]quinoline-6-carboxamide, (c) N-(4-Chlorobenzyl)-9-(3-hydroxypropyl)-7-oxo-2,3-dihydro-7H-[1,4]oxazino[2,3,4-ij]quinoline-6-carboxamide, or (d) N-(4-Chlorobenzyl)-7-oxo-9-propyl-2,3-dihydro-7H-[1,4]oxazino[2,3,4-ij]quinoline-6-carboxamide.

8. A compound of claim 1 which is N-(4-Chlorobenzyl)-9-(4-morpholinylmethyl)-7-oxo-2,3-dihydro-7H-[1,4]oxazino[2,3,4-ij]quinoline-6-carboxamide.

9. A pharmaceutical composition comprising a compound of claim 1 and a pharmaceutically acceptable excipient.

* * * * *